United States Patent [19]

Konishi et al.

[11] 4,374,662
[45] Feb. 22, 1983

[54] DIPHENYL SULFONE COMPOUNDS, AND THEIR PRODUCTION AND USE

[75] Inventors: Hiroyuki Konishi; Naganori Hino, Osaka; Hiroshi Matsumoto, Sonehigashi; Ryo Yoshida, Kawanishi, all of Japan

[73] Assignee: Sumitomo Chemical Company, Limited, Osaka, Japan

[21] Appl. No.: 318,999

[22] Filed: Nov. 6, 1981

[30] Foreign Application Priority Data

Nov. 17, 1980 [JP] Japan ................... 55-162319

[51] Int. Cl.³ .................... A01N 41/10; C07C 147/06
[52] U.S. Cl. ......................... 71/103; 560/11; 562/429; 568/33
[58] Field of Search ................ 568/33; 560/11; 562/429; 71/103

[56] References Cited

U.S. PATENT DOCUMENTS 3,426,075 2/1969 Campbell ............................. 568/49
3,957,865 5/1976 Rohe et al. .......................... 568/33
4,335,249 6/1982 Johnson et al. ..................... 560/11

OTHER PUBLICATIONS

Chemical Abstracts, 56, 8612i (1962).

*Primary Examiner*—Donald G. Daus
*Assistant Examiner*—M. C. Eakin
*Attorney, Agent, or Firm*—Birch, Stewart, Kolasch & Birch

[57] ABSTRACT

A compound of the formula:

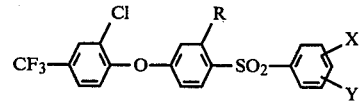

wherein R is a hydrogen atom or a lower alkoxy group and X and Y are, the same or different, each a hydrogen atom, a halogen atom, a lower alkyl group, a lower alkoxy group, a carboxy(lower)alkoxy group or a lower alkoxycarbonyl(lower)alkoxy group, which is useful as a herbicide.

11 Claims, No Drawings

DIPHENYL SULFONE COMPOUNDS, AND THEIR PRODUCTION AND USE

The present invention relates to diphenyl sulfone compounds, and their production and use. More particularly, it relates to novel diphenyl sulfone compounds bearing a 2-chloro-4-trifluoromethylphenoxy group on the benzene ring, and their preparation processes and their use as herbicides.

The said diphenyl sulfone compounds are representable by the formula:

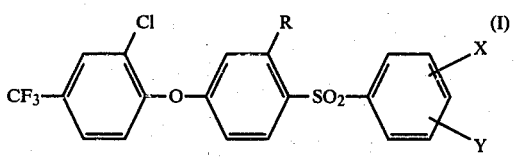

wherein R is a hydrogen atom or a lower alkoxy group and X and Y are, the same or different, each a hydrogen atom, a halogen atom, a lower alkyl group, a lower alkoxy group, a carboxy(lower)alkoxy group or a lower alkoxycarbonyl(lower)alkoxy group.

Among them, preferred are those of the formula:

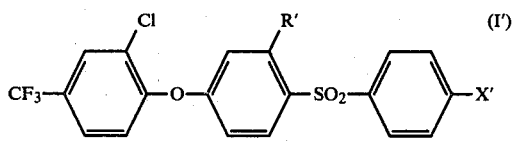

wherein R' is a lower alkoxy group and X' is a hydrogen atom, a halogen atom, a lower alkyl group or a lower alkoxy group. Particularly preferred are those of the formulas:

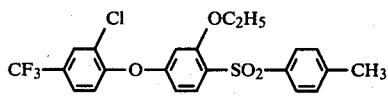

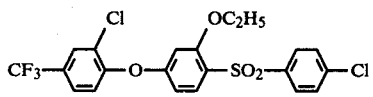

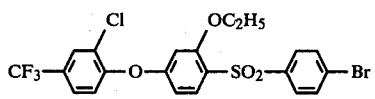

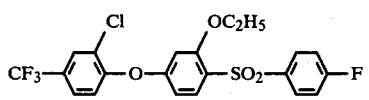

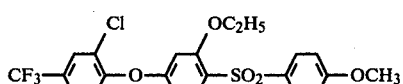

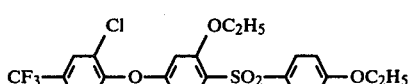

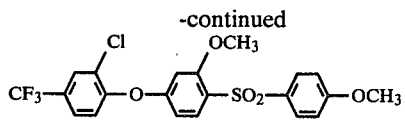

Throughout the specification, the term "lower" is intended to mean any group having not more than four carbon atoms, unless otherwise defined. The term "halogen" may include chlorine, bromine, iodine and fluorine.

Some diphenyl sulfone compounds are disclosed in Gazz. Chim. Ital., 91, 223 (1961), but this literature reference is entirely silent on whether they have any herbicidal activity.

It has now been found that the diphenyl sulfone compounds of the formula (I) exert a strong herbicidal activity against a wide variety of weeds which may cause a serious damage on important crop plants such as rice plants, corn, wheat and soybean by pre-emergence treatment as well as post-emergence treatment.

Namely, when applied to paddy fields by foliar and/or soil treatment in pre-emergence or post-emergence, the diphenyl sulfone compounds (I) can prevent and exterminate monocotyledonous weeds including Gramineae weeds such as barnyardgrass (*Echinochloa crus-galli*) and annual Cyperaceae weeds such as rice flatsedge (Cyperus sp.) and small flower umbrella plant (*Cyperus difformis*), broad-leaved weeds such as false pimpernel (*Lindernia pyxidaria*), Vandellia angustifolia, Dopatrium junceum, monochoria (*Monochoria vaginalis*), toothcup (*Rotala indica*) and Long stemmed waterwort (*Elatine triandra*), perennial weeds such as arrowhead (*Sagittaria pygmaea*), etc.

Further, when applied to farmlands by foliar and/or soil treatment in pre-emergence or post-emergence, they prevent and exterminate broad-leaved weeds such as common lambsquarters (*Chenopodium album*), velvetleaf (*Abtilon theophrasti*), tall morningglory (*Ipoea purpurea*), redroot pigweed (*Amaranthus retroflexus*) and wild buckwheat (*Polygonum convolvulus*), narrow-leaved weeds such as flatsedge (Cyperus sp.), barnyardgrass, (*Echinochloa crus-galli*), green foxtail (*Setaria viridis*), large crabgrass (*Digitaria sanguinalis*), fall panicum (*Panicum dichotomiflorum*), goosegrass (*Eleusine indica*), downy brome (*Bromus tectorum*) and quackgrass (*Aqropyron repens*), etc. At the practical dose, they do not produce any material phytotoxicity on crop plants such as rice plants, corn, wheat and barley. Thus, they are useful as herbicides applicable to paddy fields and farmlands.

Besides, due to their high herbicidal potency and broad herbicidal spectrum, they may be used as herbicides for orchards, non-agricultural fields, forests, etc.

The diphenyl sulfone compounds (I) are per se novel and may be produced by various procedures, of which typical examples are as follows:

Procedure (A)

A benzenesulfonyl halide compound of the formula:

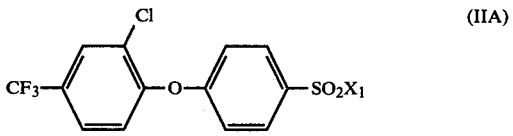

wherein $X_1$ is a halogen atom (e.g. chlorine, bromine) is reacted with a benzene compound of the formula:

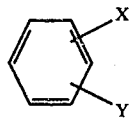  (IIIA)

wherein X and Y are each as defined above in the presence of a Lewis acid to give the diphenyl sulfone compound of the formula:

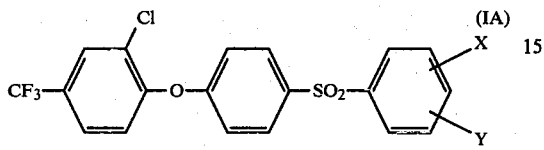  (IA)

wherein X and Y are each as defined above.

The starting benzenesulfonyl halide compound (IIA) is obtainable by reacting 2-chloro-4-trifluoromethyl-diphenyl ether with chlorosulfonic acid or by reacting 2-chloro-4-trifluoromethylphenoxybenzenesulfonic acid with a halogenating agent such as thionyl chloride or phosphorus pentachloride.

The reaction between the 2-chloro-4-trifluoromethyl-phenoxybenzenesulfonyl halide (IIA) and the benzene compound (IIIA) may be carried out in the presence of a Lewis acid as the catalyst, if necessary, in the coexistence of an inert solvent (e.g. dichloroethane, nitrobenzene, carbon disulfide), usually at a temperature of 30° to 150° C., preferably of 50° to 120° C. Examples of the Lewis acid are anhydrous ferric chloride, anhydrous tin chloride, etc. The objective diphenyl sulfone compound (IA) is obtainable in a good yield.

Procedure (B)

A diphenyl sulfide compound of the formula:

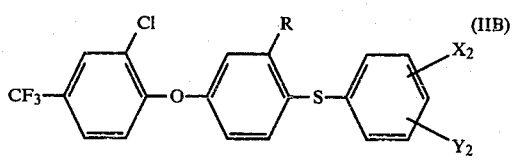  (IIB)

wherein $X_2$ and $Y_2$ are, the same or different, each a hydrogen atom, a halogen atom, a lower alkyl group or a lower alkoxy group and R is as defined above is reacted with an oxidizing agent to give the diphenyl sulfone compound of the formula:

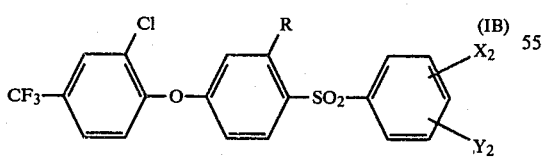  (IB)

wherein R, $X_2$ and $Y_2$ are each as defined above.

The reaction may be carried out by treatment of the diphenyl sulfide compound (IIB) with an oxidizing agent in an inert solvent (e.g. acetic acid, acetone, water) usually at a temperature of 0° to 120° C., preferably of 30° to 100° C. Examples of the oxidizing agent are hydrogen peroxide, manganese peroxide, organic peracids (e.g. peracetic acid, m-chloroperbenzoic acid), etc. The objective diphenyl sulfone compound (IB) is obtainable in a good yield.

Procedure (C)

A 1,3-diphenoxydiphenyl sulfone compound of the formula:

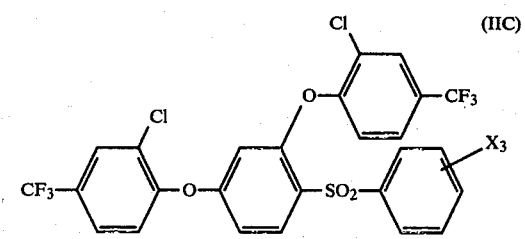  (IIC)

wherein $X_3$ is a hydrogen atom, a halogen atom, a lower alkyl group or a lower alkoxy group is reacted with an alkanol of the formula:

$R_1OH$  (IIIC)

wherein $R_1$ is a lower alkyl group in the presence of a base to give the diphenyl sulfone compound of the formula:

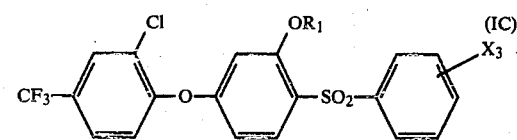  (IC)

wherein $R_1$ and $X_3$ are each as defined above.

The reaction between the 1,3-diphenoxydiphenyl sulfone compound (IIC) and the alkanol (IIIC) may be carried out in the presence of a base such as an inorganic base (e.g. sodium hydroxide, potassium hydroxide), if necessary, in the coexistence of an inert solvent (e.g. tetrahydrofuran, dioxane), usually at a temperature of 50° to 150° C., preferably of 50° to 120° C., whereby the objective diphenyl sulfone compound (IC) is obtainable in a good yield.

Among the starting materials used in the above procedures, the diphenyl sulfide compound (IIB) and the 1,3-diphenoxydiphenyl sulfone compound (IIC) are per se novel. The diphenyl sulfide compound (IIB) may be produced by reacting an aniline compound of the formula:

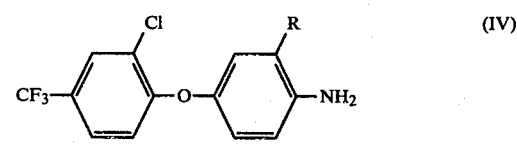  (IV)

wherein R is as defined above with a thiophenol compound of the formula:

  (V)

wherein $X_2$ and $Y_2$ are each as defined above in the manner as disclosed in Gazz. Chim. Ital., 91, 223 (1961).

The 1,3-diphenoxydiphenyl sulfone compound (IIC) may be produced by reacting a 1,3-diphenoxybenzene compound of the formula:

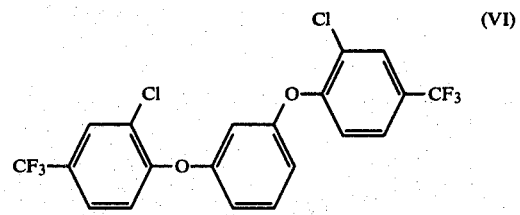

with a benzenesulfonyl compound of the formula:

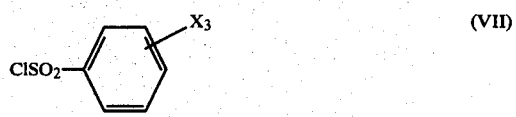

wherein $X_3$ is as defined above in an inert solvent in the presence of a Friedel-Craft catalyst. This 1,3-diphenoxybenzene compound (VI) is disclosed in Japanese Patent Publication (unexamined) No. 236/1974.

Practical embodiments of the preparation procedures as generally described above will be illustratively shown in the following Examples where % is by weight.

EXAMPLE 1

To a solution of 2-chloro-4-trifluoromethylphenoxybenzenesulfonyl chloride (2 g) in benzene (20 ml), anhydrous ferric chloride (0.96 g) was added, and the resultant mixture was refluxed for 2 hours. The reaction mixture was washed with 5% hydrochloric acid, dried over anhydrous magnesium sulfate and concentrated. The residue was crystallized from ethanol to give 2-chloro-4-trifluoromethylphenoxydiphenyl sulfone (Compound No. 1) (1.6 g). M.P., 91.5°–93° C.

EXAMPLE 2

To a mixture of 4-(2-chloro-4-trifluoromethylphenoxy)-2-ethoxyaniline (34 g), water (150 ml) and conc. hydrochloric acid (30 ml) kept at a temperature of 0° to 5° C., a solution of sodium nitrate (7.8 g) in water (30 ml) was dropwise added, and the resultant mixture was stirred for 20 minutes. This mixture was neutralized with sodium acetate and added dropwise to a mixture of powdery copper (0.3 g), p-methoxybenzenethiol (14.4 g), sodium hydroxide (4.1 g) and water (50 ml) kept at 40° C. The resulting mixture was stirred at 100° C. for 2 hours. The reaction mixture was extracted with ether. The extract was washed with 5% sodium hydroxide solution, water, 5% hydrochloric acid and water in order, dried over anhydrous magnesium sulfate and concentrated. The residual oil was chromatographed on silica gel to give 4-(2-chloro-4-trifluoromethylphenoxy)-2-ethoxy-4'-methoxydiphenyl sulfide (40 g) as an oil.

The oil was dissolved in acetic acid (200 ml), and 30% hydrogen peroxide (56 g) was dropwise added thereto at room temperature (about 25° C.) while stirring. Then, stirring was continued at 50° C. for 3 hours. To the reaction mixture, 5% sodium thiosulfate solution was added, followed by concentration. The concentrate was extracted with toluene. The extract was washed with 5% sodium hydroxide solution and water in order, dried over anhydrous magnesium sulfate and concentrated. The residual oil was chromatographed on silica gel. The obtained oil was treated with ethanol, and the precipitated crystals were recrystallized from ethanol to give 4-(2-chloro-4-trifluoromethylphenoxy)-2-ethoxy-4'-methoxydiphenyl sulfone (Compound No. 23) (11.4 g). M.P., 101°–102° C.

EXAMPLE 3

To a solution of 1,3-bis(2-chloro-4-trifluoromethylphenoxy)benzene (9 g) and p-methoxybenzenesulfonyl chloride (4.4 g) in 1,2-dichloroethane (100 ml), anhydrous ferric chloride (3.7 g) was added at room temperature, and the resultant mixture was warmed until the generation of gas ceased. The reaction mixture was admixed with 5% hydrochloric acid. The organic solvent layer was separated, washed with water and concentrated. The obtained oil was allowed to stand overnight to solidify. The resultant solid was washed with a mixture of toluene and hexane, and the resulting crystals were recrystallized from ethanol to give 1,3-bis(2-chloro-4-trifluoromethylphenoxy)-4'-methoxydiphenyl sulfone (5.3 g). M.P., 153°–155.5° C.

1,3-bis(2-chloro-4-trifluoromethylphenoxy)-4'-methoxydiphenyl sulfone (1.5 g) was dissolved in dioxane (20 ml), and a solution of potassium hydroxide (1 g) in methanol (10 ml) was added thereto while stirring. The resultant mixture was heated at 60° C. until the reaction was completed. The reaction mixture was admixed with water and extracted with toluene. The extract was washed with water, dried over anhydrous magnesium sulfate and chromatographed on silica gel, whereby 4-(2-chloro-4-trifluoromethylphenoxy)-2-methoxy-4'-methoxydiphenyl sulfone (Compound No. 25) (0.68 g) was obtained as a resinous material.

Some examples of the diphenyl sulfone compound (I) prepared in the same manner as above are shown in Table 1.

TABLE 1

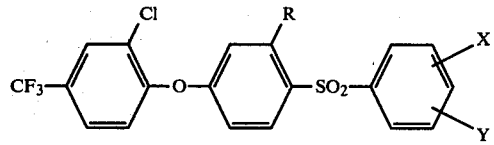

| Compound No. | R | X | Y | Physical Property | | C | H | Cl | S | Br |
|---|---|---|---|---|---|---|---|---|---|---|
| 1 | H | H | H | M.P. 91.5–93° C. | Calcd. | 55.28 | 2.93 | 8.59 | 7.77 | |
| | | | | | Found | 55.43 | 2.83 | 8.66 | 7.51 | |
| 2 | H | 4-CH$_3$ | H | M.P. 112–115° C. | Calcd. | 56.01 | 3.76 | 8.27 | 7.48 | |
| | | | | | Found | 56.28 | 3.68 | 8.37 | 7.45 | |
| 3 | H | 4-Cl | H | M.P. 86–87.5° C. | Calcd. | 51.02 | 2.48 | 15.85 | 7.17 | |

TABLE 1-continued

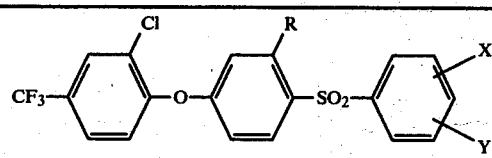

| Compound No. | R | X | Y | Physical Property | | C | H | Cl | S | Br |
|---|---|---|---|---|---|---|---|---|---|---|
| 4 | H | 4-Br | H | M.P. 87–88.5° C. | Calcd. | 46.41 | 2.25 | 7.21 | 6.52 | 16.25 |
| | | | | | Found | 46.52 | 2.07 | 7.31 | 6.34 | 16.02 |
| 5 | H | 4-F | H | M.P. 105–106.5° C. | Calcd. | 52.97 | 2.57 | 8.23 | 7.44 | |
| | | | | | Found | 53.12 | 2.60 | 7.94 | 7.33 | |
| 6 | H | 4-OCH$_3$ | H | M.P. 80.5–84° C. | Calcd. | 54.25 | 3.19 | 8.01 | 7.24 | |
| | | | | | Found | 54.17 | 3.05 | 8.17 | 7.13 | |
| 7 | H | 4-OC$_2$H$_5$ | H | M.P. 101–105° C. | Calcd. | 55.21 | 3.53 | 7.76 | 7.02 | |
| | | | | | Found | 55.37 | 3.39 | 8.06 | 6.89 | |
| 8 | H | 4-OCH$_3$ | 2-OCH$_3$ | M.P. 113–114° C. | Calcd. | 54.50 | 3.30 | 7.31 | 6.61 | |
| | | | | | Found | 54.38 | 3.40 | 7.59 | 6.36 | |
| 9 | H | 4-OC$_2$H$_5$ | 2-OC$_2$H$_5$ | M.P. 104–105° C. | Calcd. | 55.15 | 4.02 | 7.08 | 6.40 | |
| | | | | | Found | 55.20 | 4.10 | 7.15 | 6.34 | |
| 10 | H | 4-CH$_3$ | 2-OCH$_3$ | M.P. 103.5–105° C. | Calcd. | 55.21 | 3.53 | 7.76 | 7.02 | |
| | | | | | Found | 55.23 | 3.37 | 7.96 | 6.87 | |
| 11 | H | 4-OCH$_3$ | 2-CH$_3$ | M.P. 100–101° C. | Calcd. | 55.21 | 3.53 | 7.76 | 7.02 | |
| | | | | | Found | 55.16 | 3.45 | 8.01 | 7.20 | |
| 12 | H | 4-OCHCOOCH$_3$ (CH$_3$) | H | Resinous | Calcd. | 53.65 | 3.52 | 6.89 | 6.23 | |
| | | | | | Found | 53.70 | 3.51 | 6.95 | 6.08 | |
| 13 | H | 4-OCHCOOC$_3$H$_7$(n) (CH$_3$) | H | $n^{26}$ 1.5454 | Calcd. | 55.30 | 4.08 | 6.53 | 5.91 | |
| | | | | | Found | 55.57 | 3.92 | 6.76 | 5.68 | |
| 14 | H | 4-OCHCOOH (CH$_3$) | H | Resinous | Calcd. | 52.76 | 3.22 | 7.08 | 6.40 | |
| | | | | | Found | 52.53 | 3.19 | 6.85 | 6.58 | |
| 15 | H | 4-OCH$_2$COOCH$_3$ | H | M.P. 136.5–137.5° C. | Calcd. | 52.76 | 3.22 | 7.08 | 6.40 | |
| | | | | | Found | 52.89 | 3.51 | 6.79 | 6.12 | |
| 16 | OC$_2$H$_5$ | H | H | M.P. 116.5–117.5° C. | Calcd. | 55.21 | 3.53 | 7.76 | 7.02 | |
| | | | | | Found | 55.31 | 3.49 | 8.02 | 6.88 | |
| 17 | OC$_2$H$_5$ | 4-CH$_3$ | H | M.P. 116–117.5° C. | Calcd. | 56.12 | 3.85 | 7.53 | 6.81 | |
| | | | | | Found | 55.91 | 3.76 | 7.72 | 6.52 | |
| 18 | OC$_2$H$_5$ | H | 3-CH$_3$ | M.P. 127–128.5° C. | Calcd. | 56.12 | 3.85 | 7.53 | 6.81 | |
| | | | | | Found | 56.14 | 3.63 | 7.52 | 6.75 | |
| 19 | OC$_2$H$_5$ | H | 2-CH$_3$ | M.P. 139–141° C. | Calcd. | 56.12 | 3.85 | 7.53 | 6.81 | |
| | | | | | Found | 56.07 | 3.77 | 7.57 | 7.07 | |
| 20 | OC$_2$H$_5$ | 4-Cl | H | M.P. 105.5–107° C. | Calcd. | 51.34 | 3.08 | 14.43 | 6.35 | |
| | | | | | Found | 51.62 | 3.05 | 14.39 | 6.12 | |
| 21 | OC$_2$H$_5$ | 4-Br | H | M.P. 110.5–115° C. | Calcd. | 47.08 | 2.82 | 6.62 | 5.98 | 14.91 |
| | | | | | Found | 47.04 | 2.80 | 6.33 | 5.61 | 14.78 |
| 22 | OC$_2$H$_5$ | 4-F | H | M.P. 142–144.5° C. | Calcd. | 53.12 | 3.18 | 7.47 | 6.75 | |
| | | | | | Found | 53.19 | 3.20 | 7.56 | 6.56 | |
| 23 | OC$_2$H$_5$ | 4-OCH$_3$ | H | M.P. 101–102° C. | Calcd. | 54.27 | 3.73 | 7.28 | 6.59 | |
| | | | | | Found | 54.33 | 3.61 | 7.06 | 6.47 | |
| 24 | OC$_2$H$_5$ | 4-OC$_2$H$_5$ | H | Resinous | Calcd. | 55.15 | 4.02 | 7.08 | 6.40 | |
| | | | | | Found | 54.92 | 3.83 | 7.32 | 6.47 | |
| 25 | OCH$_3$ | 4-OCH$_3$ | H | Resinous | Calcd. | 53.34 | 3.41 | 7.50 | 6.78 | |
| | | | | | Found | 53.46 | 3.25 | 7.54 | 7.06 | |

In the practical usage of the diphenyl sulfone compound (I), it may be applied as such or in any preparation form as conventionally adopted in the related art field (e.g. dust, crude dust, fine granule, granule, wettable powder, emulsifiable concentrate, flowable, solution, suspension).

For formulation of said preparations, solid or liquid carriers or diluents may be used. The terms "carriers and diluents" as herein used are intended to mean natural or synthetic organic or inorganic substances which are used in a mixture with the active ingredient in order to assist the reach and contact of the active ingredient to the part to be treated and/or to make easy the storage, transportation and treatment of the active ingredient.

The dust may usually comprise the active ingredient in a solid carrier in a concentration of about 1 to 25% by weight. The wettable powder comprises normally the active ingredient in a solid carrier and a dispersing or wetting agent optionally with a protective colloidal agent, a thixotropic agent, an antifoaming agent, etc. in a concentration of about 25 to 90% by weight. The granules may comprise the active ingredient in a solid carrier in a concentration of about 0.5 to 35% by weight, the active ingredient being uniformly dispersed in the carrier or being fixed or adsorbed evenly at the surfaces of the carrier, and have a particle size of about 0.2 to 1.5 mm. The emulsifiable concentrate may include normally the active ingredient in a liquid carrier comprising about 5 to 20% by weight of an emulsifier in a concentration of about 5 to 50% by weight.

As for the solid carrier or diluent, there may be exemplified mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like. As for the liquid carrier or diluent, there may be exemplified alcohols (e.g. methanol, n-hexanol, ethylene glycol, diethylene glycol, cyclohexanol, benzyl alcohol), ether alcohols (e.g. ethylene glycol ethyl ether, ethylene glycol phenyl ether, diethylene glycol ethyl ether, diethylene glycol butyl ether), paraffinic or naphthenic hydrocarbons (e.g. kerosene, mineral oil, spindle oil, white oil), aromatic hydrocarbons (e.g. benzene, toluene, xylene, ethylbenzene, cumene, methylnaphthalene), halogenated hydrocarbons (e.g. carbon tetrachloride, chloroform, trichloroethylene, monochlorobenzene, o-chlorotoluene), ethers (e.g. dioxane, tetrahydrofuran), ketones (e.g. acetone, methylethylketone, diisobutylketone, cyclohexanone, acetophenone, isophorone), esters (e.g. ethyl acetate, amyl acetate, ethylene glycol acetate, diethylene glycol acetate, dibutyl maleate, diethyl succinate), dimethylformamide, dimethylsulfoxide, water, etc.

A surface active agent used for emulsifying, dispersing, wetting, spreading, binding, break-controlling, stabilizing, flowability-improving, rust-preventing, etc. may be any of the non-ionic, anionic, cationic and ampholeric type of agents. Examples of the non-ionic surface active agent are additive polymerization products of ethylene oxide to higher alcohols (e.g. lauryl alcohol, stearyl alcohol, oleyl alcohol), additive polymerization products of ethylene oxide to alkylphenols (e.g. isooctylphenol, nonylphenol), additive polymerization products of ethylene oxide to alkylnaphthols (e.g. butylnaphthol, octylnaphthol), additive polymerization products of ethylene oxide to higher fatty acids (e.g. palmitic acid, stearic acid, oleic acid), additive polymerization products of ethylene oxide to monoalkyl or dialkyl phosphates (e.g. stearyl phosphate, dilauryl phosphate), additive polymerization products of ethylene oxide to amines (e.g. dodecylamine, stearylamide), higher fatty acid esters of polyvalent alcohols (e.g. sorbitan) and additive polymerization products of ethylene oxide thereto, additive polymerization products of ethylene oxide and propylene oxide, etc. Examples of the anionic surface active agent are alkylsulfates (e.g. sodium laurylsulfate, amine salts of oleyl alcohol sulfuric esters), alkylsulfonates (e.g. sodium sulfosuccinic acid dioctyl ester, sodium 2-ethylhexylsulfonate), arylsulfonates (e.g. sodium isopropylnaphthalenesulfonate, sodium methylenebisnaphthalenesulfonate, sodium ligninsulfonate, sodium dodecylbenzenesulfonate), etc.

Besides, any other auxiliary agent(s) may be used in order to improve the properties of the preparations and enhance the biological effect of the preparations. Examples of the auxiliary agent are casein, gelatin, albumin, glue, sodium alginate, carboxymethylcellulose, methylcellulose, hydroxyethylcellulose, polyvinyl alcohol, etc.

In the herbicidal composition of this invention, the content of the diphenyl sulfone compound (I) as the active ingredient may be usually from 0.1 to 95% by weight, preferably from 0.5 to 90% by weight, although its favorable content varies within a wide range depending upon the type of formulation as hereinbefore stated.

Practical embodiments of the herbicidal composition according to the invention are illustratively shown in the following Examples wherein part(s) and % are by weight.

FORMULATION EXAMPLE 1

In a mixer, Compound No. 5 (4 parts), clay (66 parts) and bentonite (30 parts) are mixed uniformly. To the mixture, a suitable amount of water is added, and the resulting mixture is kneaded in a kneader. The resultant mixture is extruded through a screen of 0.8 mm in mesh size, and the extruded granules are dried in a dryer at 50° C. to give a granule containing 4% of the active ingredient.

FORMULATION EXAMPLE 2

In a mixer, Compound No. 23 (2 parts), clay (90 parts), talc (3 parts) and sodium ligninsulfonate (5 parts) are mixed uniformly. After addition of a suitable amount of water, the resultant mixture is kneaded in a kneader and then extruded through a screen of 0.8 mm in mesh size, followed by drying in a dryer at 50° C. to give a granule containing 2% of the active ingredient.

FORMULATION EXAMPLE 3

Compound No. 20 (50 parts), clay (30 parts), diatomaceous earth (10 parts), white carbon (5 parts) and sodium alkylbenzenesulfonate (5 parts) are pulverized and mixed well to give a wettable powder containing 50% of the active ingredient.

FORMULATION EXAMPLE 4

Compound No. 24 (20 parts), xylene (45 parts) and "Sorpol SM100" (a surface active agent manufactured by Toho Kagaku K.K.) (15 parts) are mixed together to give an emulsifiable concentrate containing 20% of the active ingredient.

The dosage of the herbicide of the invention depends upon the kind of the active ingredient, the sort of the cultivated plants, the method of application, the weather, etc. When, for instance, the herbicide is applied to paddy fields or farmlands in pre-emergence or post-emergence of weeds by soil treatment, its amount may be from about 5 to 2000 grams (as the active ingredient) per 10 ares. In order to exterminate weeds in non-agricultural fields such as roads and play grounds, its amount may be from about 20 to 4000 grams (as the active ingredient) per 10 ares.

The diphenyl sulfone compound (I) may be used together with other herbicides to improve its activity as the herbicide, and in some cases, to produce a synergistic effect. As the herbicides to be mixed therewith, there may be mentioned triazine series herbicides such as 2-methylthio-4,6-bisethylamino-1,3,5-triazine, 2-chloro-4,6-bisethylamino-1,3,5-triazine, 2-methylthio-4-ethylamino-6-(1,2-dimethylpropyl)amino-s-triazine, 2-methoxy-4-ethylamino-6-isopropylamino-1,3,5-triazine, 2-chloro-4-ethylamino-6-isopropylamino-s-triazine, 2-methylthio-4,6-bis(isopropylamino)-s-triazine, 2-methylthio-4-ethylamino-6-isopropylamino-s-triazine, 4-amino-6-tert.-butyl-3-(methylthio)-1,2,4-triazin-5(4H)-one; phenoxy series herbicides such as 2,4-dichlorophenoxyacetic acid and its methyl, ethyl or butyl ester, 4-chloro-2-methylphenoxyacetic acid, ethyl 2-methyl-4-chlorophenoxybutylate; diphenyl ether series herbicides such as 2,4,6-trichlorophenyl-4'-nitrophenyl ether, 2,4-dichlorophenyl-4'-nitrophenyl ether, 2,4-dichlorophenyl-4'-nitro-3'-methoxyphenyl ether; urea series herbicides such as 3-(3,4-dichlorophenyl)-1-methoxy-1-methylurea, 3-(3,4-dichlorophenyl)-1,1-dimethylurea, 1-(α,α-dimethylbenzyl)-3-(4-tolyl)urea, N-[4-(4-methylphenethyloxy)phenyl]-N'-methyl-N'-methoxyurea, 3-(4-chlorophenyl)-1,1-dimethylurea; carbamate series herbicides such as 3-methoxycarbonylaminophenyl N-(3-methylphenyl)carbamate, isopropyl N-(3-chlorophenyl)carbamate, methyl N-(3,4-dichlorophenyl)carbamate; uracil series herbicides such as 5-bromo-3-sec.-butyl-6-methyluracil, 1-cyclohexyl-3,5-propylene uracil; thiol carbamate series herbicides such as S-(4-chlorobenzyl) N,N-diethylthiolcarbamate, S-ethyl N-cyclohexyl-N-ethylthiolcarbamate, S-ethyl hexahydro-1H-azepin-1-carbothioate, S-ethyl N,N-di-n-propylthiolcarbamate; pyridinium chloride series herbicides such as 1,1'-dimethyl-4,4'-bispyridinium dichloride; phosphorus series herbicides such as N-(phosphonomethyl)glycin, O-ethyl-O-(2-nitro-5-methylphenyl)-N-sec.-butylphosphoroamidothioate; aniline series herbicides such as α,α,α-trifluoro-2,6-dinitro-N,N-dipropyl-p-toluidine, 4-(methylsulfonyl)-2,6-dinitro-N,N-dipropylaniline; acid anilide series herbicides such as 2-chloro-2',6'-diethyl-N-(butoxymethyl)acetanilide, n-butyl-N-chloroacetyl-2,6-diethylanilinoacetate, 2-chloro-2',6'-diethyl-N-(methoxymethyl)acetanilide, 3,4-dichloropropionanilide, N-(α,α-dimethylbenzyl)-α-bromo-tert.-butylacetamide; 5-tert.-butyl-3-(2,4-dichloro-5-isopropoxyphenyl)-1,3,4-oxadiazolin-2-one; 2-(α-naphthoxy)-N,N-diethylpropionamide; 1,3-dimethyl-4-(2,4-dichlorobenzoyl)-5-pyrazolyl-p-toluenesulfonate; 3-isopropyl-benzo-2-thia-1,3-diazinon-(4)-2,2-dioxide; 3-(2-methylphenoxy)-pyridazine, etc.

The herbicides of the invention may be applied together with fungicides, microbial pesticides, pyrethroidal insecticides, other insecticides, plant growth regulators, fertilizers, etc.

Some test examples which show the herbicidal activity of the diphenyl sulfone compound (I) are shown in the following Examples wherein % is by weight.

EXAMPLE I

Into polyethylene-made pots of 70 cm² in surface area, paddy field soil was filled. Seeds of barnyardgrass (*Panicum crus-galli*) and broad-leaved weeds such as monochoria, false pimpernel, toothcup and *Dopatrium junceum* were mixed into the soil. The pots were flooded with water to make a paddy field condition. In each of the pots, two bulbs of arrowhead were planted. Then, rice plants at the two or three foliate stage were transplanted into the pots. Cultivation was carried out in a greenhouse at 25° to 30° C. On the 2nd day after the transplantation, the test compound formulated in an emulsifiable concentrate and diluted with water was applied to the pots in an amount of 10 ml per pot by soil treatment. Cultivation was further continued in the greenhouse. On the 25th day from the soil treatment, the herbicidal effect and the phytotoxicity were determined on the following criteria:

Herbicidal effect:

| Evaluation | Prevention percentage (%) |
|---|---|
| 0 | 0–19 |
| 1 | 20–39 |
| 2 | 40–59 |
| 3 | 60–79 |
| 4 | 80–99 |
| 5 | 100 (completely dead) |

Phytotoxicity to rice plants:

| Evaluation | Remarks |
|---|---|
| 0 | No phytotoxicity |
| 1 | Slight phytotoxicity observed but no material influence on growth |
| 2 | Growth once influenced but recovered; no material reduction in crop |
| 3 | Growth and crop slightly influenced |
| 4 | Growth and crop influenced |
| 5 | Completely dead |

The results are shown in Table 2.

TABLE 2

| Compound No. | Dosage (weight of active ingredient, g/are) | Herbicidal activity Barnyard-grass | Broad-leaved weed | Arrow-head | Phyto-toxicity Rice plant |
|---|---|---|---|---|---|
| 1 | 5 | 3 | 5 | 5 | 0 |
|   | 10 | 5 | 5 | 5 | 0 |
| 2 | 5 | 4 | 5 | 5 | 0 |
|   | 10 | 5 | 5 | 5 | 0 |
| 4 | 2.5 | 5 | 5 | 5 | 0 |
|   | 5 | 5 | 5 | 5 | 0 |
| 5 | 5 | 3 | 5 | 5 | 0 |
|   | 10 | 4 | 5 | 5 | 0 |
| 6 | 2.5 | 5 | 5 | 3 | 0 |
|   | 5 | 5 | 5 | 4 | 0 |
| 8 | 2.5 | 5 | 5 | 5 | 0 |
|   | 5 | 5 | 5 | 5 | 0 |
| 10 | 5 | 4 | 5 | 3 | 0 |
|   | 10 | 5 | 5 | 4 | 0 |
| 11 | 5 | 3 | 5 | 4 | 0 |
|   | 10 | 4 | 5 | 5 | 0 |
| 13 | 10 | 3 | 5 | 5 | 0 |
|   | 20 | 5 | 5 | 5 | 0 |
| 14 | 10 | 3 | 5 | 5 | 0 |
|   | 20 | 4 | 5 | 5 | 0 |
| 16 | 5 | 5 | 5 | 3 | 0 |
|   | 10 | 5 | 5 | 4 | 0 |
| 17 | 10 | 5 | 5 | 2 | 0 |
|   | 20 | 5 | 5 | 4 | 0 |
| 18 | 10 | 5 | 5 | 2 | 0 |
|   | 20 | 5 | 5 | 4 | 0 |
| 20 | 10 | 5 | 5 | 2 | 0 |
|   | 20 | 5 | 5 | 4 | 0 |
| 21 | 5 | 5 | 5 | 3 | 0 |
|   | 10 | 5 | 5 | 4 | 0 |
| 22 | 10 | 5 | 5 | 2 | 0 |
|   | 20 | 5 | 5 | 4 | 0 |
| 23 | 2.5 | 5 | 5 | 5 | 0 |
|   | 5 | 5 | 5 | 5 | 0 |
| 25 | 2.5 | 5 | 5 | 5 | 0 |
|   | 5 | 5 | 5 | 5 | 0 |
| Control (a)*(1) | 2.5 | 1 | 2 | 0 | 0 |
|   | 5 | 3 | 4 | 1 | 0 |
| Control (b)*(2) | 2.5 | 0 | 1 | 0 | 0 |
|   | 5 | 2 | 4 | 0 | 0 |
| Control (c)*(3) | 5 | 4 | 4 | 0 | 0 |
|   | 10 | 4 | 4 | 0 | 0 |

Note
*(1) 2,4-Dichlorophenyl-4'-nitro-3'-methoxyphenyl ether
*(2) 2,4,6-Trichlorophenyl-4'-nitro-phenyl ether
*(3) 4-(4-chlorophenoxy)-4'-chloro-diphenyl sulfone

EXAMPLE II

Into polyethylene-made trays of 700 cm² in surface area, farmland soil was filled. Seeds of corn, rice plant and wheat as well as seeds of common lambsquarters, velvetleaf, tall morningglory, redroot pigweed, wild buckwheat and black nightshade (*Solanum nigrum*) were sowed therein. Two to three weeks thereafter, the test compound formulated in an emulsifiable concentrate and diluted with water was sprayed to the trays in an amount of 5 liters per are by foliar treatment. On the 20th day after the foliar treatment, the herbicidal effect and the phytotoxicity were determined as in Example I.

The results are shown in Table 3.

TABLE 3

| Compound No. | Dosage (weight of active ingredient, g/are) | Herbicidal activity | | | | | | Phytotoxicity | | |
|---|---|---|---|---|---|---|---|---|---|---|
| | | Common lambs-quarters | Velvet-leaf | Tall morning-glory | Redroot pigweed | Wild buck-wheat | Black night-shade | Rice plant | Corn | Wheat |
| 3 | 5 | 4 | 5 | 4 | 5 | 5 | 5 | 0 | 0 | 0 |
|   | 10 | 5 | 5 | 5 | 5 | 5 | 5 | 0 | 0 | 0 |
| 9 | 5 | 3 | 5 | 5 | 5 | 2 | 3 | 0 | 0 | 0 |
|   | 10 | 4 | 5 | 5 | 5 | 4 | 4 | 0 | 0 | 0 |
| 23 | 2.5 | 5 | 5 | 5 | 5 | 5 | 5 | 0 | 0 | 0 |
|    | 5 | 5 | 5 | 5 | 5 | 5 | 5 | 0 | 0 | 0 |
| 24 | 2.5 | 5 | 5 | 5 | 5 | 5 | 5 | 0 | 0 | 0 |
|    | 5 | 5 | 5 | 5 | 5 | 5 | 5 | 0 | 0 | 0 |
| Control (a) | 2.5 | 2 | 1 | 1 | 1 | 0 | 5 | 1 | 1 | 1 |
|             | 5 | 4 | 4 | 4 | 3 | 3 | 5 | 1 | 1 | 1 |
| Control (c) | 2.5 | 0 | 0 | 0 | 0 | 0 | 0 | 0 | 0 | 0 |
|             | 5 | 0 | 0 | 0 | 0 | 0 | 0 | 0 | 0 | 0 |
| Untreated | — | 0 | 0 | 0 | 0 | 0 | 0 | 0 | 0 | 0 |

EXAMPLE III

Into plastic trays (35×25×10 cm), farmland soil was filled, and seeds of common purslane (*Portulaca oleracea*), corn and soybean were sowed, followed by covering with the soil. The test compound formulated in an emulsifiable concentrate and diluted with water was applied to the trays in an amount of 3 liters per are by spraying over the top. Cultivation was continued in a greenhouse for 20 days. Then, the herbicidal effect and the phytotoxicity were determined as in Example I.

The results are shown in Table 4.

TABLE 4

| Compound No. | Dosage (weight of active ingredient, g/are) | Herbicidal activity Common purslane | Phytotoxicity | |
|---|---|---|---|---|
| | | | Corn | Soybean |
| 8 | 10 | 5 | 0 | 0 |
|   | 20 | 5 | 0 | 0 |
| 17 | 10 | 5 | 0 | 0 |
|    | 20 | 5 | 0 | 0 |
| 23 | 10 | 5 | 0 | 0 |
|    | 20 | 5 | 0 | 0 |
| Control (c) | 10 | 0 | 0 | 0 |
| Control (d)*(1) | 10 | 2 | 0 | 0 |
|                 | 20 | 4 | 0 | 0 |
| Untreated | — | 0 | 0 | 0 |

Note:
*(1)2,4-Dichlorophenyl-3'-methoxy-carbonyl-4'-nitrophenyl ether

EXAMPLE IV

Into plastic trays (35×25×10 cm), farmland soil was filled, and seeds of soybean, redroot pigweed, velvetleaf, cocklebur (*Xanthium pensylvanicum*), tall morningglory and jimsonweed (*Datura stramonium*) were sowed. After being cultivated outdoors for 17 days, every two trays were placed in a frame of 50 cm long, 100 cm wide and 40 cm high, and the test compound formulated in an emulsifiable concentrate comprising a spreading agent and diluted with water to make 25 ml was applied thereto by spraying over the top. At this stage, the plants were generally at the 1 to 4 foliar stage and of 2 to 20 cm in height. Cultivation was further continued outdoors for 3 weeks. Then, the herbicidal effect and the phytotoxicity were determined as in Example I.

The results are shown in Table 5.

TABLE 5

| Compound No. | Dosage (weight of active ingredient g/are) | Phyto-toxicity Soybean | Herbicidal activity | | | | |
|---|---|---|---|---|---|---|---|
| | | | Redroot pigweed | Velvet-leaf | Cocklebur | Tall morning-glory | Jimsonweed |
| 23 | 10 | 1 | 5 | 5 | 5 | 5 | 5 |
|    | 3  | 0 | 5 | 5 | 5 | 5 | 5 |
|    | 1  | 0 | 5 | 5 | 4 | 5 | 5 |
| 24 | 10 | 1 | 5 | 5 | 5 | 5 | 5 |
|    | 3  | 1 | 5 | 5 | 5 | 5 | 5 |
|    | 1  | 0 | 5 | 5 | 4 | 4 | 5 |
| 25 | 10 | 1 | 5 | 5 | 5 | 5 | 5 |
|    | 3  | 1 | 5 | 5 | 5 | 5 | 5 |
|    | 1  | 0 | 5 | 5 | 5 | 5 | 5 |
| Control (e)*(1) | 10 | 1 | 5 | 5 | 5 | 5 | 5 |
|                 | 3  | 1 | 5 | 5 | 4 | 5 | 5 |
|                 | 1  | 0 | 5 | 5 | 4 | 5 | 5 |

Note:
*(1)Commercially available herbicide known as "Acifluorfen", which is representable by the formula:

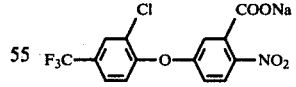

What is claimed is:

1. A compound of the formula:

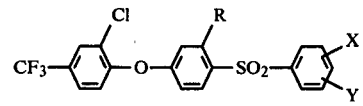

wherein R is a hydrogen atom or a lower alkoxy group and X and Y, being the same or different, are each a hydrogen atom, a halogen atom, a lower alkyl group, a lower alkoxy group, a carboxy(lower)alkoxy group or a lower alkoxycarbonyl(lower)alkoxy group.

2. The compound according to claim 1, which is represented by the formula:

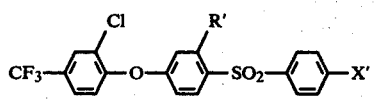

wherein R' is a lower alkoxy group and X' is a hydrogen atom, a halogen atom, a lower alkyl group or a lower alkoxy group.

3. The compound according to claim 1, which is represented by the formula:

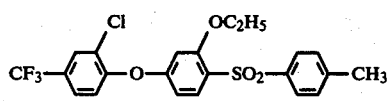

4. The compound according to claim 1, which is represented by the formula:

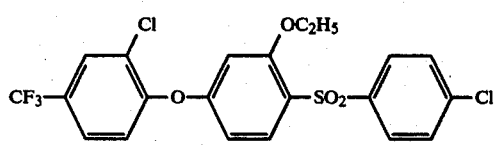

5. The compound according to claim 1, which is represented by the formula:

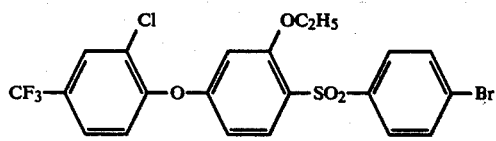

6. The compound according to claim 1, which is represented by the formula:

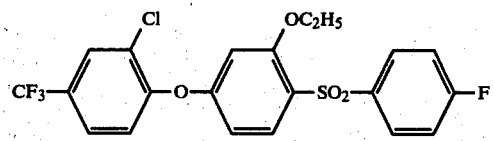

7. The compound according to claim 1, which is represented by the formula:

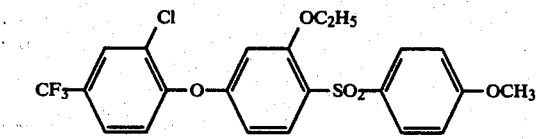

8. The compound according to claim 1, which is represented by the formula:

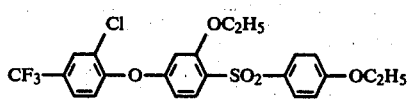

9. The compound according to claim 1, which is represented by the formula:

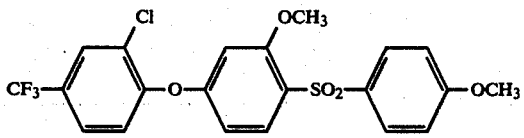

10. A herbicidal composition which comprises as an active ingredient a herbicidally effective amount of the compound according to claim 1 and an inert carrier or diluent.

11. A method for preventing or exterminating weeds which comprises applying a herbicidally effective amount of the compound according to claim 1 to the area where the weeds grow or will grow.

* * * * *